United States Patent [19]
Piuk et al.

[11] Patent Number: 6,060,020
[45] Date of Patent: May 9, 2000

[54] METHOD AND APPARATUS FOR TREATING OBJECTS WITH OZONE

[75] Inventors: Vladimir Piuk; Mark Shnaiderman, both of Kiryat Yam, Israel

[73] Assignee: S.P.M. Recovery Technologies Ltd, Haifa, Israel

[21] Appl. No.: 09/057,790

[22] Filed: Apr. 9, 1998

[51] Int. Cl.$^7$ .................................. A61L 2/24; A61L 2/20
[52] U.S. Cl. .......................... 422/33; 422/292; 73/49.3; 604/25
[58] Field of Search .......................... 422/33, 292; 312/1; 73/49.3; 604/25

[56] References Cited

U.S. PATENT DOCUMENTS

| | | |
|---|---|---|
| 3,907,389 | 9/1975 | Cox et al. .................................... 312/1 |
| 5,052,382 | 10/1991 | Wainwright . |
| 5,098,415 | 3/1992 | Levin . |
| 5,259,895 | 11/1993 | Sharp .................................... 73/49.3 X |
| 5,334,355 | 8/1994 | Faddis .................................... 422/30 X |
| 5,868,999 | 2/1999 | Karlson .................................... 422/30 |
| 5,951,948 | 9/1999 | Duroselle et al. .................................... 422/33 |

*Primary Examiner*—Elizabeth McKane
*Attorney, Agent, or Firm*—Graham & James LLP; Rashida A. Karmali

[57] ABSTRACT

A method and apparatus for treating an object with ozone by: introducing the object to be treated and ozone into a sealed treatment chamber; and applying a negative pressure to said treatment chamber to prevent ozone leaking from said treatment chamber into the atmosphere and to provide an indication of the condition of the seal. The object may be treated according to a Static mode, or a Flow mode.

30 Claims, 5 Drawing Sheets

METHOD AND APPARATUS FOR TREATING OBJECTS WITH OZONE

FIELD OF THE INVENTION

The present invention relates to a method and apparatus for treating objects with ozone.

BACKGROUND OF THE INVENTION

Ozone is increasingly being used for treating both inanimate objects, such as water supplies, food products, and the like, e.g., for sterilization purposes, as well as animate objects, such as body parts of animals or of human beings for the promotion of healing. The beneficial effects of treatment with ozone in promoting healing are now well recognized. Examples of know ozone-treating methods and apparatus and applications therefor, are described in U.S. Pat. Nos. 5,052,382 and 5,098,415.

Ozone, however, is a dangerous material and can raise a serious health hazard if not handled properly. Thus, a quantity of as little as 0.01 ppm (parts per million) of ozone in the atmosphere can be sensed by human beings, and a concentration of greater than 0.1 ppm is regarded as being extremely dangerous. When it is appreciated that ozone treatment processes frequently involve concentrations of as high 50,000 ppm, it will be seen that the smallest leak of ozone to the atmosphere can create a very real health danger to anyone in the immediate vicinity.

SUMMARY OF THE INVENTION

An object of the present invention is to provide an ozone treatment method, and also an ozone treatment apparatus, substantially reducing the health hazard present with ozone treatments. Another object of the invention is to provide a method and apparatus which may be used for administering ozone treatments to both animate and inanimate objects in an efficient and effective manner.

According to one aspect of the present invention, there is provided a method of treatog an object with ozone comprising introducing the object to be treated and ozone into a sealed treatment chamber; and applying a negative pressure to the treatment chamber to prevent ozone leaking from the treatment chamber into the atmosphere and to provide an indication of the condition of the seal.

According to another aspect of the invention, there is provided a method of treating an object with ozone comprising, introducing the object to be treated, and a fluid mixture including ozone, into a treatment chamber; and treating the object in the treatment chamber in a static mode under conditions in which there is no flow of ozone into or out of the chamber except that tests are performed at testing intervals wherein, for each test, an outflow from the chamber is produced, the outflow is tested for any drop in ozone content, and a quantity of fresh ozone is introduced into the chamber to make-up for any drop of ozone content therein.

According to a further aspect of the invention, there is provided a method of treating an object with ozone, comprising: introducing the object to be treated into a sealed treatment chamber; applying a positive pressure to the treatment chamber; making pressure measurements to determine the drop of positive pressure within the chamber; applying a negative pressure to the chamber; making pressure measurements to determine the drop of negative pressure within the chamber; and if both the positive and negative pressure drops are within predetermined acceptable limits, introducing ozone into the chamber to treat the object therein.

According to a still further aspect of the invention, there is provided an apparatus for treating an object with ozone, comprising: a sealed treatment chamber for receiving the object, the treatment chamber including an inlet for introducing an ozone mixture therein, and an outlet for removing the ozone mixture therefrom; a supply of ozone connected to the inlet of the treatment chamber; a suction pump connected to the outlet of the treatment chamber; and a control system for controlling the ozone supply and the suction pump to produce a negative pressure in the treatment chamber in order to prevent ozone leakage from the chamber into the atmosphere and to provide an indication of the condition of the seal.

According to a yet further aspect of the invention, there is provided an is apparatus for treating an object with ozone, comprising: an air-impermeable housing of a hollow construction to define a treatment chamber, the housing being formed with an inlet and outlet for ozone, and with an opening for introducing the object to be treated into the treatment chamber; a flexible air-impermeable sleeve having one end lining the opening and the opposite end extending externally of the treatment chamber; and a clamping ring clamping the one end of the sleeve to the housing.

As will be described more particularly below, the method and apparatus of the present invention may be used for administering ozone treatments in a manner which substantially reduces or eliminates the health hazard presented by even extremely low concentrations of ozone in the air. In addition, the method and apparatus of the present invention can be used for administering ozone in an efficient and effective manner, both to animate objects for promoting healing, as well as to inanimate objects, such as water or food products, for sterilizing or other purposes.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

The Overall Construction

The preferred embodiment of the invention described below is for administering an ozone treatment to a body part, such as a person's foot, in order to promote healing. The apparatus includes a sealed treatment chamber illustrated in FIG. 1 for receiving the object (person's foot) to be treated; and a control system as illustrated in FIG. 2 for supplying the ozone to the treatment chamber and for controlling its delivery in order to make the treatment effective, as well as to decrease the possibility of leakage of ozone to the atmosphere which could create a serious health danger, and to provide an indicator of the condition of the seal.

Figure 1:
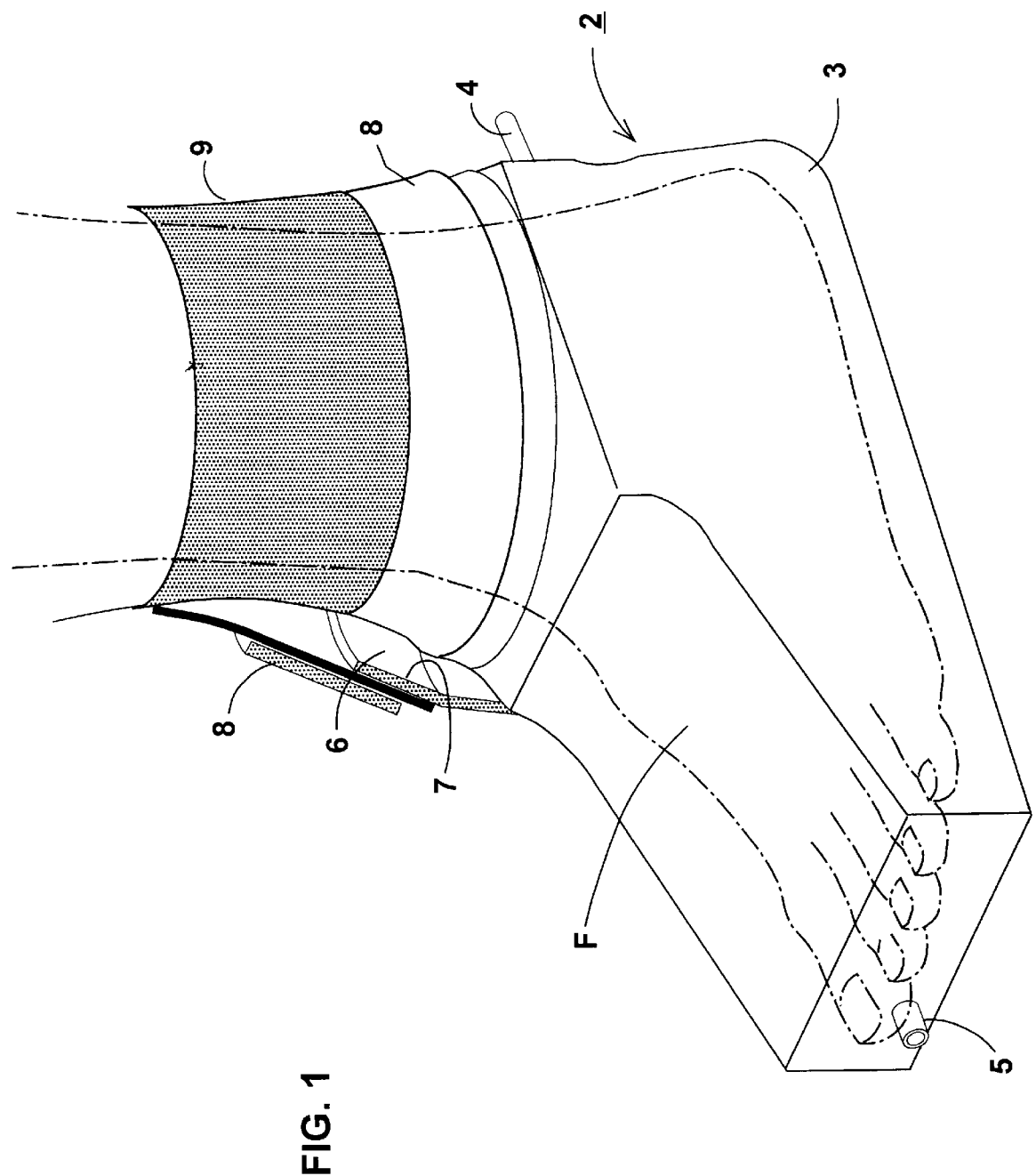
FIG. 1 illustrates one form of treatment chamber constructed in accordance with the present invention for use in apparatus to treating an object with ozone.
Figure 2:
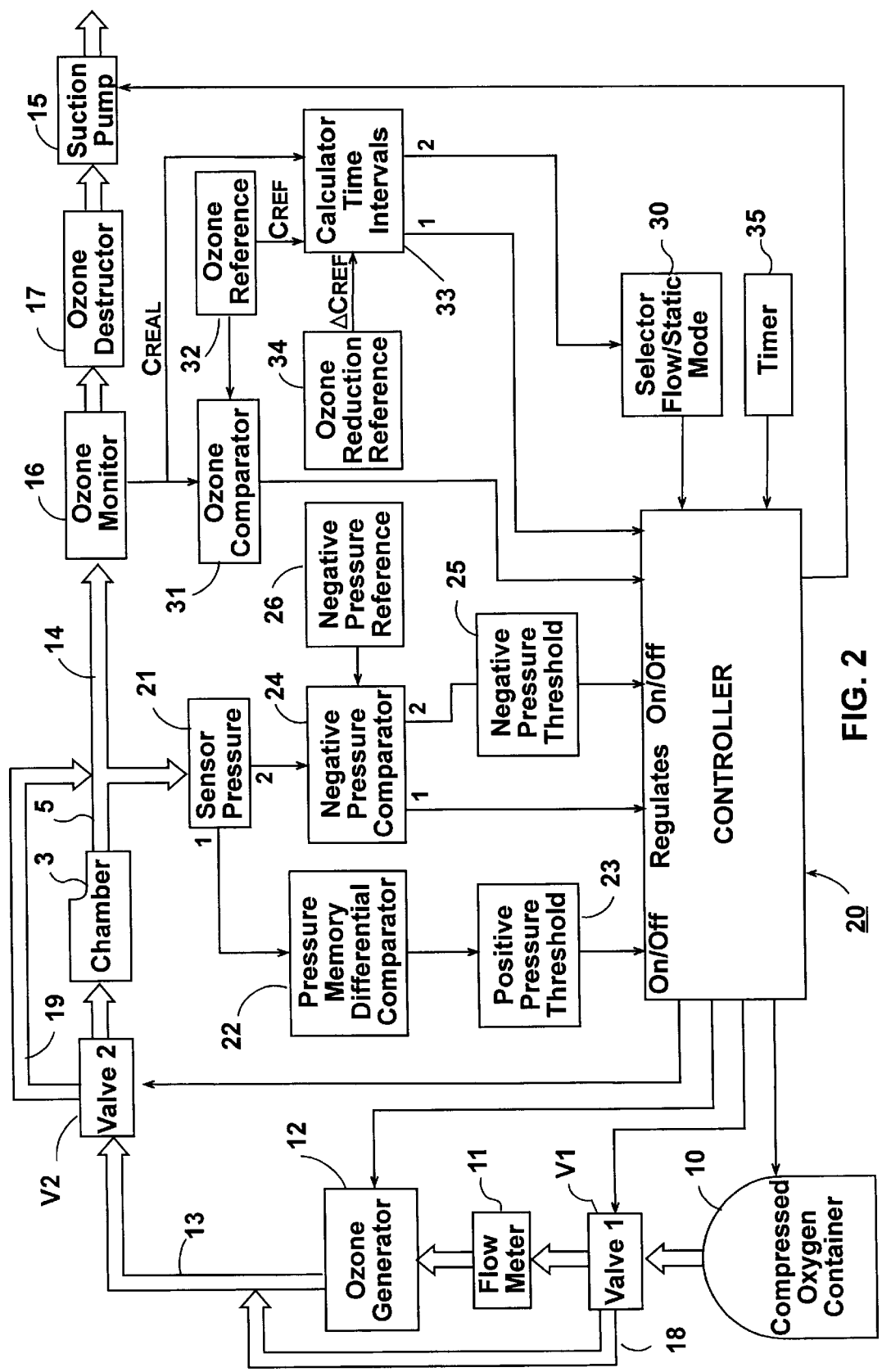
FIG. 2 illustrates the overall system to be used with the treatment chamber of FIG. 1.

The apparatus illustrated in FIG. 1, comprises a rigid air-impermeable housing 2 of a hollow construction to define the treatment chamber 3 within it of a configuration to receive the foot F to be treated. Treatment chamber 3 includes an inlet 4 at one end for introducing the ozone, and an outlet 5 at the opposite end for removing the ozone. As described below, the ozone is in the form of a mixture with oxygen. Preferably, the mixture includes 95–98% oxygen and about 2–5% ozone.

Housing 2 is further formed with enlarged opening 6 for receiving the foot F to be treated. Opening 6 is circumscribed by an annular collar 7 having an outer surface of conical configuration complementary to the conical configuration of the inner surface of a locking ring 8. One end of a flexible, air-impermeable sleeve 9 is interposed between collar 7 and clamping ring 8 and is clamped in place by pressing collar 8 downwardly to produce a friction fit with collar 7. The opposite end of sleeve 9 extends outwardly of housing 2.

Preferably, sleeve 9 is of an elastic material so that the outer end of the sleeve firmly the grips the ankle of the person's foot to be treated, thereby providing a hermetic seal with respect to the treatment chamber 3 within housing 2. Alternatively, sleeve 9 may be of a pliable plastic material, in which case the external end of the sleeve should be firmly clamped against the subject's ankle by the application of the another clamping ring or band (not shown).

The Ozone Supply and Control System

The supply of the ozone/oxygen mixture to the treatment chamber 3 within housing 2 is shown in FIG. 2. It includes a container of compressed oxygen 10 connected, via a valve $V_1$ and a flow meter 11, to an ozone generator 12. The ozone generator 12, which may be of a known construction, is connected by a connecting line 13 and a second valve $V_2$ to the inlet 4 of the treatment chamber 3. The outlet 5 of the treatment chamber is connected by a line 14 to a suction pump 15 for discharge, after the ozone/oxygen mixture has passed through an ozone monitor 16 and an ozone destructor 17.

The ozone supply and control system illustrated in FIG. 2 further includes a bypass line 18 from valve $V_1$ to the outlet end of the ozone generator 12 for bypassing the ozone generator. A second bypass line 19 connected from valve $V_2$ to the outlet end of treatment chamber 3 bypasses the treatment chamber.

The overall control is effected by a controller, generally designated 20. As will be described more particularly below, controller 20 controls the suction pump 15, valve $V_1$, ozone generator 12, and valve $V_2$. Bypass line 18 and control valve $V_1$ permit the controller 20 to cause only pure oxygen, or an ozone/oxygen mixture of the required concentration, to be delivered to the treatment chamber 3. Bypass line 19 and control valve $V_2$ permit controller 20 to measure the pressure drop within chamber 3. This is done by first operating valve $V_2$ to direct all the flow through the bypass 19 to the outlet end of chamber 3, and then operating valve $V_2$ to direct all the flow through the chamber 3. These two operations enable measurements to be made of the pressure drop through the chamber.

A pressure sensor 21 is provided at the outlet end of the treatment chamber 3 to measure the pressure thereat. As will be described below, the pressure is measured at the outlet end of chamber 3 during an initial testing mode, to test the seal against leakage from the treatment chamber to the atmosphere, and also during an operational mode, to maintain a preterminted negative pressure within the treatment chamber. The initial testing mode is effected under both positive pressure and negative pressure conditions. Therefore, pressure sensor 21 is connected to the controller 20 via a positive pressure comparator 22 and a positive pressure threshold presetting device 23, and also via a negative pressure comparator 24 and a negative pressure threshold presetting device 25. The negative pressure during the operational mode is preset by negative pressure reference device 26. The outputs of the positive pressure threshold device 23, the negative pressure comparator 24, and the negative pressure threshold device 25, are fed-back to the controller 20.

As will also be described more particularly below, controller 20 may be operated according to a Static operational mode, or a Flow operational mode, as preselected by a mode selector 30. During both operational modes, the ozone concentration in the mixture outletfed from treatment chamber 3 is continuously monitored by ozone monitor 16, which supplies feedback signals to controller 20 for controlling the ozone generator 12.

The illustrated system is operated mostly in the Static operational mode. In such a mode, there is no flow into or out of the treatment chamber 3. A normal treatment is generally for a period of 20–30 minutes. Since ozone is relatively unstable, the concentration of the ozone within the treatment chamber continuously diminishes during this treatment period. The rate of diminishment is not easily predetermined since it depends upon many factors, such as temperature, humidity conditions, etc.

Ozone treatment for healing wounds is generally optimum when the ozone concentration is between 2–5% of the ozone/oxygen mixture. Thus, if the treatment starts out with a 5% ozone concentration, during the course of the treatment the concentration could diminish so as to substantially reduce the effectiveness of the treatment. During the Flow operational mode, ozone monitor 16 continuously monitors the ozone concentration, and controls the ozone generator 12 to maintain the optimum ozone/oxygen concentration. However, since there is no flow in the Static operational mode, the ozone concentration cannot be detected by the ozone monitor 16 unless a flow is produced through the outlet of the treatment chamber 3.

As will be described below, such a flow is produced during the Static mode after a pretermined time interval following the start of the treatment, (e.g., 2–5 minutes), and the concentration of ozone is measured. Controller 20 determines the quantity of make-up ozone to be applied to restore the original concentration. The controller also utilizes the magnitude of the make-up quantity to determine the next testing time. Thus, if only a small make-up quantity of ozone is needed to restore the optimum concentration, the next time for testing will be at a longer time interval than if a large make-up quantity of ozone is required. If intervals between tests become too short, controller 20 is automatically switched-over from the Static to the Flow mode.

For accomplishing the latter functions, the illustrated system includes an ozone comparator 31 for comparing the actual ozone concentration ($C_{REAL}$) as detected by the ozone monitor 16 with a reference concentration ($C_{REF}$) inputted at 32. The illustrated system further includes a calculator 33 for calculating from $\Delta C_{REF}$ (the make-up ozone to restore the original concentration) the time interval for the next testing period, and an ozone reduction reference input device 34 for inputting the initial time interval. The outputs of the ozone comparator 31 and the time interval calculator 33 are fed-back to the controller 20.

The Operation

Figure 3A:
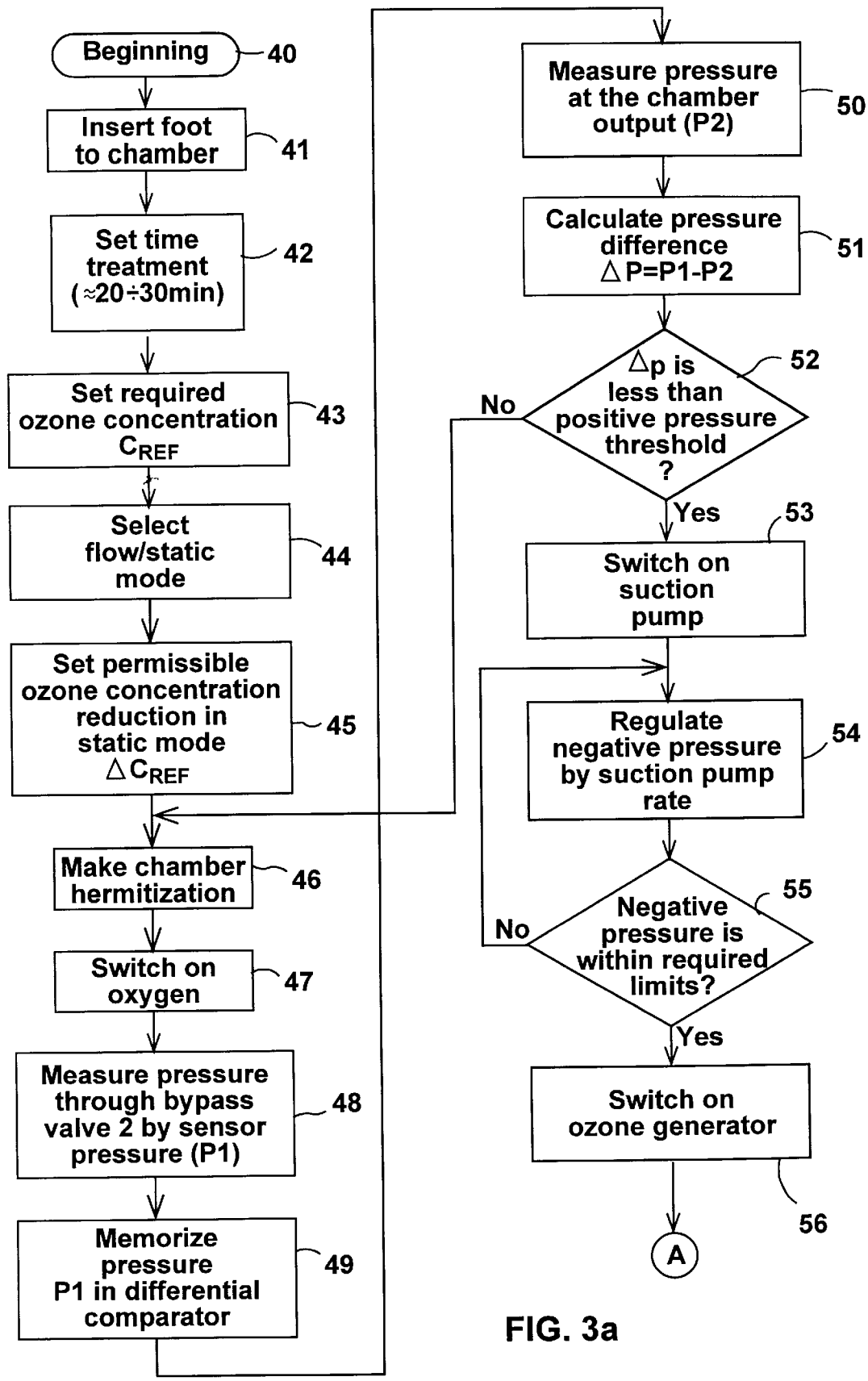
FIGS. 3a–3c are charts illustrating a preferred mode of operation of the system of FIG. 2.
Figure 3B:
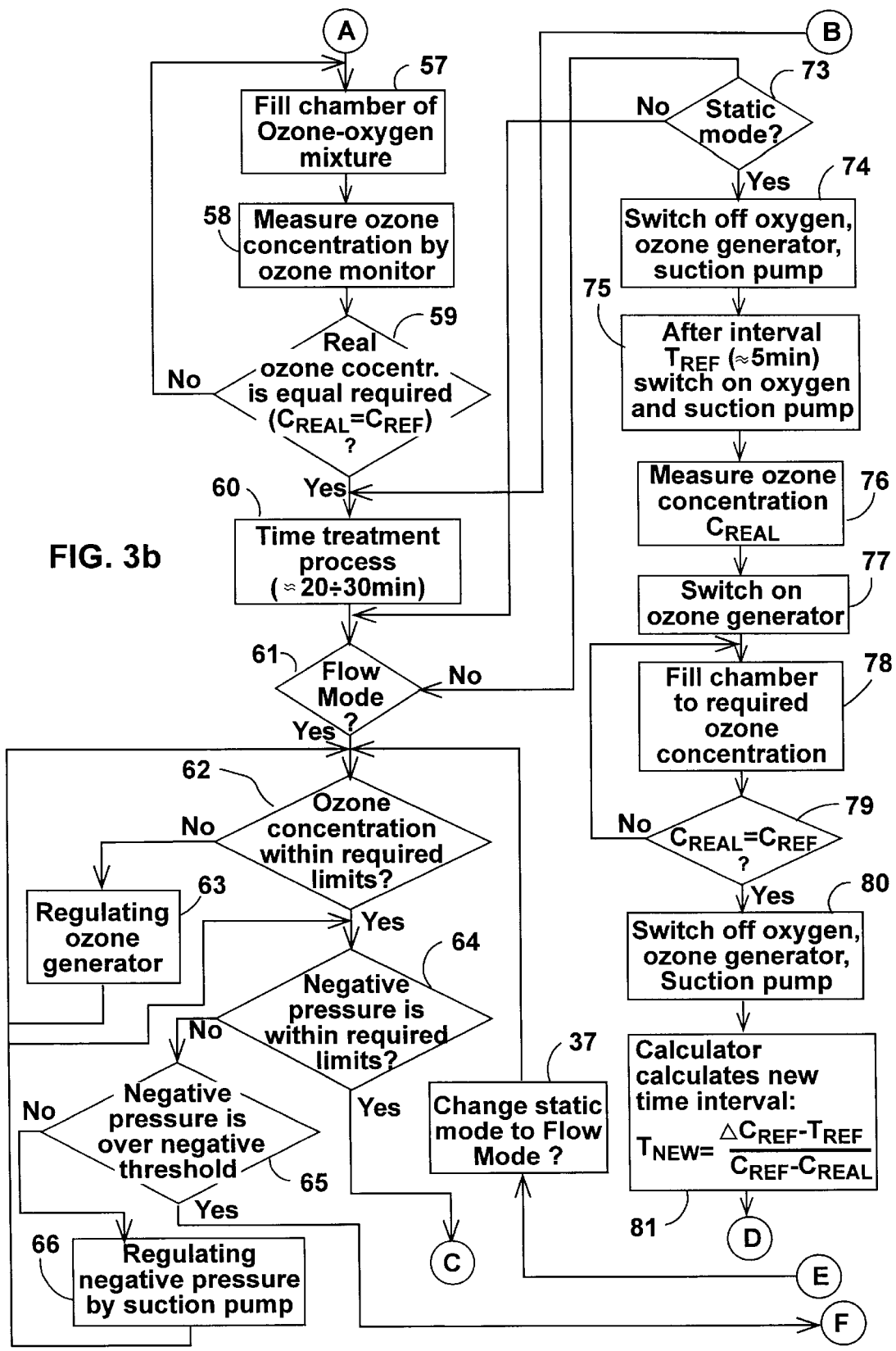
Figure 3C:
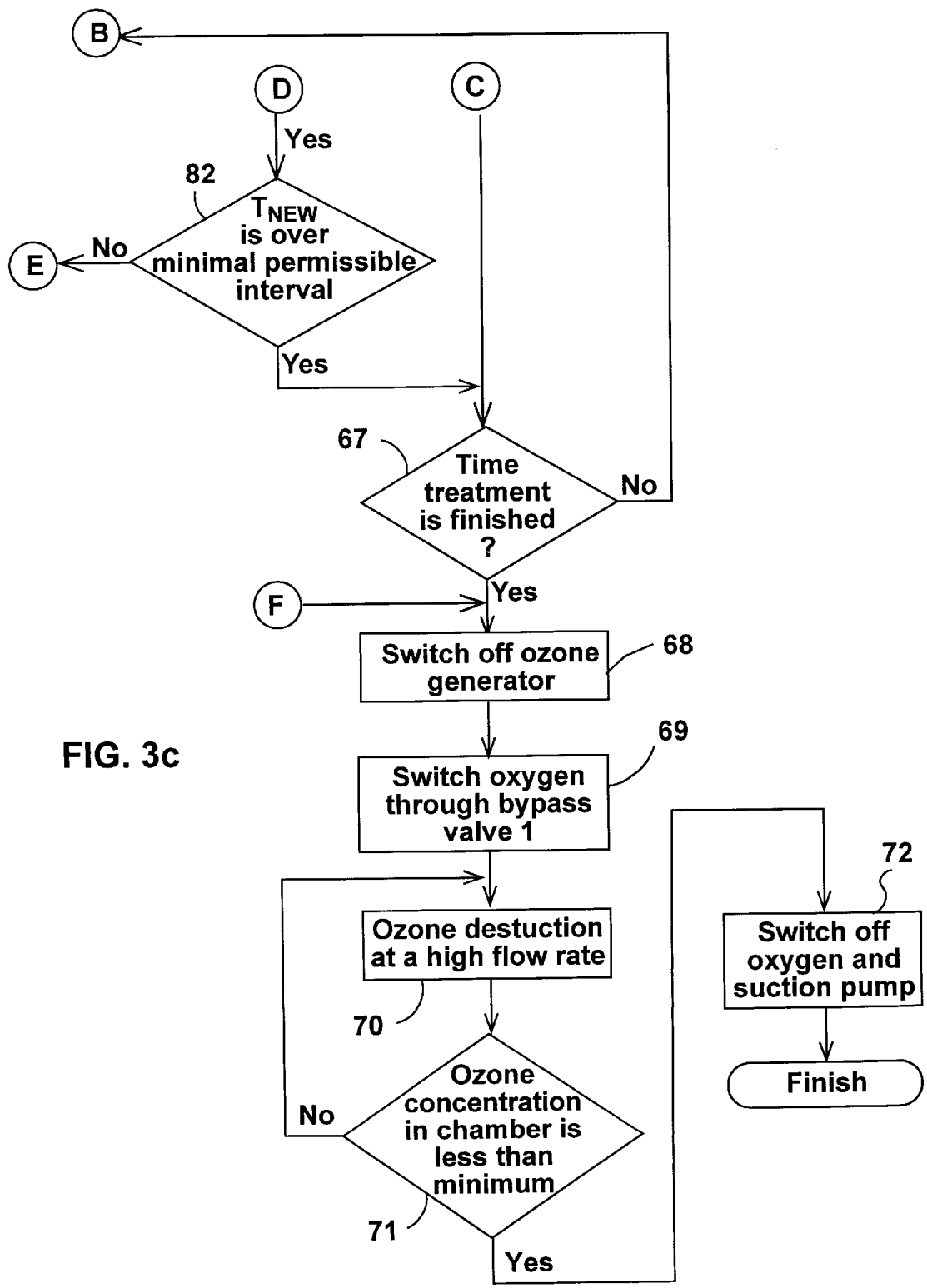

The overall operation of the apparatus illustrated in FIGS. 1 and 2 will now be described particularly with reference to the flow charts of FIGS. 3a and 3b.

After the subject inserts the foot to be treated into the treatment chamber 3 (block 41), timer 35 of controller 20 is set for the treatment time, e.g. 20–30 minutes (block 42). The desired ozone concentration ($C_{ref}$) is also preset via reference device 32 (block 43), and the mode selector 30 is then preset for either the Static or Flow mode of operation (block 44). If the Static mode is selected, the permissible reduction in the ozone concentration ($\Delta c_{ref}$) is set via device 34 (block 45).

The treating chamber 3 is then hermetically sealed by securing clamping ring 8 with a friction fit to collar 7 of housing 2. The lower end of the gas-impermeable sleeve 9 is thus clamped between ring 8 and collar 7, and the upper end of the sleeve tightly grips the subject's ankle as shown in FIG. 1. The treatment chamber 3 is thus hermetically sealed (block 46). An initial test of the seal of treating chamber 3 is then made, as follows:

First, valve $V_1$ is controlled to conduct the oxygen from container 10 towards the treatment chamber 3, bypassing the ozone generator 12 (block 47). Then, valve $V_2$ is controlled to conduct the oxygen to the outlet end of treatment chamber 3, where it is sensed by pressure sensor 21 (block 48); this provides a measurement of pressure ($P_1$), corresponding to the pressure at the inlet of the treatment chamber. This pressure is recorded in the memory of comparator 22 (block 49).

Valve $V_2$ is then controlled to direct the oxygen into the inlet of the treatment chamber 3, and the pressure at the outlet ($P_2$) is again sensed by pressure sensor 21 and recorded in the memory of comparator 22 (block 50). Controller 20 then calculates the pressure drop ($\Delta P$) experienced in the treatment chamber 3 by the oxygen applied to that chamber under positive pressure (block 51) and determines whether or not $\Delta P$ is too high (block 52). If it is too high, this means that the treatment chamber has not been adequately sealed, which requires that the seal be improved and then returning to step 46.

If $\Delta P$ is within the permissible threshold, the software makes a negative-pressure check of the seal of the treatment chamber 3 by turning on the suction pump 15, regulating the negative pressure applied by the suction pump to the treatment chamber 3 (block 54), and assuring that the negative pressure is within the required limits (block 55). If so, this indicates that the treatment chamber 3 is adequately sealed, thereby completing the initial testing mode.

When this initial testing mode has been completed, the ozone generator 12 is turned on (block 56); valve $V_1$ is controlled to direct the oxygen from container 10 to the ozone generator 12; and valve $V_2$ is controlled to direct the resulting ozone/oxygen mixture into the treatment chamber 3 (block 57). The ozone concentration at the outlet 5 of the treatment chamber is measured by ozone monitor 16 (block 58), and a determination is made whether the real ozone concentration ($C_{REAL}$) is equal to that required ($C_{REF}$) (block 59). If not, the ozone generator 12 is controlled until the required concentration is attained.

The treatment time is then preset by timer 35 (FIG. 2), e.g. for a 20–30 minute treatment period (block 60). A check is made to determine whether the controller is in the Flow or Static mode of operation (block 61).

If in the Flow mode, the ozone/oxygen mixture is continuously supplied to the treatment chamber 3 while the ozone monitor 16 continuously checks the ozone concentration (block 62), and controls the ozone generator 12 (block 63) to maintain the ozone concentration within the required limits. During the Flow mode, the pressure sensor 21 also senses negative pressure at the outlet of the treatment chamber 3 and checks whether the negative pressure is within the required limits (block 64), and is over the negative pressure threshold (block 65) fixed by the negative pressure threshold device 25. Controller 20 controls the suction pump 15 (block 66) to maintain the negative pressure within the required limits, preferably 5–10 mm Hg below atmosphere The foregoing Flow mode of operation is continued until the preset treatment time is completed (block 67), whereupon the ozone generator 12 is switched off (block 68), valve $V_1$ is actuated to conduct the oxygen through the bypass 18 and through the treating chamber 3 to exhaust the ozone within that chamber (block 69), and the ozone destructor 17 is actuated at a high rate (block 70) to convert the ozone to oxygen at a high rate. This continues until ozone monitor 16 senses that the ozone within in the treatment chamber 3 is below a pretermined minimum (block 71), whereupon valve $V_1$ is actuated to switch-off the supply of oxygen, and the suction pump 15 is turned-off by the controller (block 72).

If when the mode check was made (block 61), it was determined that the controller is in the Static mode (block 73), the oxygen the ozone generator 12, and the suction pump 15 are all switched off (block 74), and the object within the treatment chamber 3 is subjected to a static ozone/oxygen treatment.

After a predetermined time interval (e.g. 2–5 minutes), a test is made to determine the ozone concentration within the treatment chamber 3 to assure that the ozone concentration has not unduly dropped because of its unstability and is still within the prescribed range ($\Delta C_{REF}$). To make this test, valve $V_1$ is controlled to direct the oxygen flow through the ozone generator 12 and into the treatment chamber 3 while the suction pump 15 is energized. The ozone concentration at the outlets of the treatment chamber is measured by ozone monitor 16 (block 76). The ozone generator 12 is switched-on (block 77), to fill the treatment chamber 3 with make-up ozone/oxygen mixture until the concentration is found to be within the prescribed limits (block 79), at which time the oxygen, ozone generator, and suction pump are switched off (block 80). A calculation is then made to determine the time interval for the next time for testing according to the make-up ozone added to the treatment chamber 3 (block 81).

The foregoing Static mode treatment is continued, and the next time interval for testing is computed according to the amount of make-up ozone supplied, as described above. Whenever the next time for testing is found to be below a pretermined value, the controller automatically switches-over to the Continuous mode of treatment (block 82).

While the invention has been described with respect to one preferred embodiment, it will be appreciated that this is set forth merely for purposes of example, and that many other variations, modifications and applications of the invention may be made.

What is claimed is:

1. An apparatus for treating an object with ozone, comprising:
   a treatment chamber for receiving the object, said treatment chamber being hermetically sealing means to provide a complete seal, said treatment chamber including an inlet for introducing an ozone-oxygen mixture therein, and an outlet for removing the ozone mixture therefrom;
   a supply of ozone-oxygen connected to the inlet of said treatment chamber;

a suction pump connected to the outlet of said treatment chamber;

a sealing check means for testing the sealing means;

and a control system for controlling said ozone-oxygen supply, said suction pump to produce a negative pressure in said treatment chamber in order to prevent ozone leakage from the chamber into the atmosphere and the sealing check means to provide an indication of the condition of the seal;

wherein said control system is a means for producing a static mode of operation, wherein there is no ozone flow into or out from said treatment chamber except during testing periods wherein a flow is produced through the outlet and the loss in ozone is determined and is made-up by introducing a quantity of make-up ozone via the inlet of said treatment chamber.

2. The apparatus according to claim 1, wherein said ozone supply includes a source of oxygen, an ozone generator connected to the oxygen source to receive oxygen and to generate ozone therefrom, a connecting line connecting the outlet of the ozone generator to the inlet of said treatment chamber, and a line by-passing said ozone generator and connecting said oxygen source directly to said connecting line;

and wherein said control system further includes a valve, said valve being controlled by a controller for selectively directing the oxygen from said oxygen source either to the inlet to said ozone generator or to the outlet from said ozone generator via said bypass line.

3. The apparatus according to claim 2, wherein said ozone supply system further includes a second by-pass line connected to said connecting line and by-passing said treatment chamber;

and wherein said control system further includes a second valve controlled by said controller for selectively directing the ozone/oxygen mixture to the inlet or to the outlet of said treatment chamber.

4. The apparatus according to claim 3, wherein said control system further includes a pressure sensor for sensing the pressure at the outlet from said treatment chamber, and for inputting a control signal to said controller in response thereto.

5. The apparatus according to claim 4, wherein said control system further includes an ozone sensor for sensing the ozone at the outlet of said treatment chamber, and for inputting another control signal to said controller in response thereto.

6. The apparatus according to claim 5, wherein said apparatus further includes an ozone destructor between said ozone sensor and said suction pump.

7. The apparatus according to claim 1, wherein said treatment chamber comprises:

an air-impermeable housing of a hollow construction to define said treatment chamber, said housing being formed with said inlet and outlet for said ozone, and with an opening for introducing into said treatment chamber the object to be treated;

a flexible air-impermeable sleeve having one end lining said opening and its opposite end extending externally of said treatment chamber within the housing;

and a clamping ring clamping said one end of the flexible sleeve to said housing.

8. The apparatus according to claim 7, wherein said clamping ring is of a conical configuration and is receivable with a friction fit over a complementary conical section of the housing circumscribing said opening therein with the one end of the flexible sleeve clamped between the conical ring and the conical section of the housing.

9. The apparatus according to claim 7, wherein said sleeve is of a flexible elastic material and its outer end firmly grips the object.

10. The apparatus according to claim 7, wherein said flexible sleeve is of a pliable plastic material, and the apparatus further includes a second clamping ring for clamping the outer end of the pliable sleeve to the object.

11. The apparatus according to claim 1, wherein the control system includes a scaling analyzer having an inlet port and an outlet port, a controller having an inlet port and an outlet port, wherein the inlet port of the sealing analyzer is connected to the outlet port of the sealing check means and, the outlet port of the sealing analyzer is connected to the inlet port of the controller to check pressure within the treatment chamber.

12. The apparatus according to claim 11 wherein the sealing analyzer further includes a pressure memory differential comparator, the comparator being capable of calculating the pressure difference at the inlet and at the outlet of the treatment chamber.

13. The apparatus according to claim 12, wherein the controller is programmed to start an ozone treatment depending on the pressure change in the oxygen flow, and the controller is programmed to interrupt an ozone.

14. The apparatus according to claim 13, wherein the treatment depending on the pressure change in the oxygen-ozone flow, apparatus further includes an ozone monitor between the treatment chamber and the suction pump, the ozone monitor being capable of monitoring the ozone concentration in the treatment chamber.

15. The apparatus according to claim 1, wherein the treatment chamber is defined by an air-impermeable housing of a hollow construction, said housing having an inlet and an outlet for ozone, and an opening for introducing an object to be treated, in the treatment chamber a flexible air-impermeable sleeve having one end lining the opening and an opposite end extending external to the treatment chamber, and a clamping ring clamping one end of the flexible sleeve to the housing.

16. The apparatus according to claim 15, wherein the clamping ring is of a conical configuration, said clamping ring is receivable with a friction fit over a complementary conical section of the housing, such that one end of the flexible sleeve is clamped between the conical ring and the conical section of the housing.

17. The apparatus according to claim 15, wherein the sleeve consists of an elastic material, and one end of the sleeve firmly grips the object.

18. The apparatus according to claim 15, wherein the sleeve consists of a pliable plastic material, and the apparatus further includes a second clamping ring for clamping one end of the pliable plastic sleeve to the object.

19. The apparatus according to claim 1, wherein the treatment chamber is designed to house objects of varying shapes and sizes, said objects comprising limbs, toes, arms, hands, shoulders, neck or head.

20. An apparatus for treating an object with ozone, comprising;

a treatment chamber for receiving the object, said treatment chamber being hermetically sealed by a sealing means to provide a complete seal, said treatment chamber including an inlet for introducing an ozone-oxygen mixture therein, and an outlet for removing the ozone mixture therefrom;

a supply of ozone-oxygen connected to the inlet of said treatment chamber;

a suction pump connected to the outlet of said treatment chamber;

a sealing check means for testing the sealing means;

and a control system for controlling said ozone-oxygen supply, said suction pump to produce a negative pressure in said treatment chamber in order to prevent ozone leakage from the chamber into the atmosphere and the sealing check means to provide an indication of the condition of the seal, wherein said control system includes a controller programmed to measure the magnitude of the make-up ozone introduced into the treatment chamber.

21. Apparatus for treating an object with ozone, comprising:

an air-impermeable housing of a hollow construction to define a treatment chamber, said housing being formed with an inlet and an outlet for ozone, and with an owning for introducing the object to be treated into said treatment chamber;

a flexible air-impermeable elastic sleeve having one end lining said opening and the opposite end extending externally of said treatment chamber;

and a clamping ring clamping said one end of the flexible air-impermeable sleeve to said air-impermeable housing, wherein clamping ring is of a conical configuration and is receivable with a friction fit over a complementary conical section of the air-impermeable housing circumscribing said opening therein, with the one end of the flexible air-impermeable sleeve clamped between the conical ring and the conical section of the air-impervious housing.

22. The apparatus according to claim 21, wherein said sleeve of the flexible elastic material and its opposite end firmly grips the object.

23. The apparatus according to claim 21, further including a second clamping ring for firmly clamping the external portion of the pliable plastic sleeve to the object.

24. A method of treating an object with ozone comprising:

introducing the object to be treated and ozone into a treatment chamber and hermetically sealing the chamber with a sealing means;

and applying a negative pressure to said treatment chamber to prevent ozone leaking from said treatment chamber into the atmosphere and to provide an indication of the condition of the seal using a checking means, wherein said object is treated in said treatment chamber in a Static mode in which there is no flow into or out of said chamber, except the tests are performed at testing intervals wherein, for each test, an outflow is produced from the chamber, the outflow is tested for any drop in ozone content, and a quantity of fresh ozone is introduced into the chamber to make-up for any drop of ozone content therein.

25. The method according to claim 24, wherein the magnitude of the quantity of make-up ozone introduced into said treatment chamber during one test determines the time interval until the next test is performed, the larger the make-up quantity, the smaller the time interval for the next test.

26. A method of treating an object with ozone comprising:

introducing the object to be treated and ozone into a treatment chamber and hermetically sealing the chamber with a sealing means;

and applying a negative pressure to said treatment chamber to prevent ozone leaking from said treatment chamber into the atmosphere and to provide an indication of the condition of the sealing means using a checking means;

wherein, before said ozone is introduced into said treatment chamber a positive pressure is applied to said chamber, and pressure measurements are made to determine the drop of positive pressure within said chamber, to provide thereby an indication of whether the sealing condition of the treatment chamber is satisfactory for the treatment to be made; and wherein the drop in pressure in said treatment chamber is determined by measuring the pressure at the output of said treatment chamber (a) while directing the positive pressure through said treatment chamber, and (b) while directing the positive pressure to a bypass around said treatment chamber.

27. A method of treating an object with ozone, comprising:

introducing the object to be treated and a fluid mixture including ozone into a treatment chamber and hermetically sealing the chamber with a sealing means;

and treating the object in said treatment chamber in a Static mode under conditions in which there is no flow of ozone into or out of said chamber except that tests are performed at testing intervals wherein, for each test, an outflow from the chamber is produced, the outflow is tested for any drop in ozone content, and a quantity of fresh ozone is introduced into the chamber to make-up for any drop of ozone content therein.

28. The method according to claim 27, wherein the magnitude of the quantity of make-up ozone introduced into said treatment chamber during one test determines the time interval for performing the next test, the larger the make-up quantity, the smaller the time interval for the next test.

29. The method according to claim 28, wherein the time intervals between the periods between tests are monitored, and when such a time interval drops below a predetermined value, the treatment is automatically changed-over to a Flow mode in which there is a continuous flow of the mixture including the ozone into and out said treatment chamber.

30. The method according to claim 27, wherein a negative pressure is applied to said treatment chamber during the treatment of the object therein to prevent ozone leaking from the chamber into the atmosphere.

* * * * *